United States Patent
Tamayo De Miguel et al.

(10) Patent No.: US 9,829,427 B2
(45) Date of Patent: Nov. 28, 2017

(54) METHOD AND SYSTEM FOR CHARACTERIZATION OF NANO- AND MICROMECHANICAL STRUCTURES

(71) Applicant: CONSEJO SUPERIOR DE INVESTIGACIONES CIENTIFICAS (CSIC) [ES/ES], Madrid (ES)

(72) Inventors: Francisco Javier Tamayo De Miguel, Madrid (ES); Valerio Pini, Madrid (ES); Priscila Monteiro Kosaka, Madrid (ES); Montserrat Calleja Gomez, Madrid (ES); Sheila Gonzalez Castilla, Madrid (ES)

(73) Assignee: Consejo Superior De Investigaciones Cientificas (CSIC), Madrid (ES)

( * ) Notice: Subject to any disclaimer, the term of this patent is extended or adjusted under 35 U.S.C. 154(b) by 323 days.

(21) Appl. No.: 14/406,007

(22) PCT Filed: May 23, 2013

(86) PCT No.: PCT/ES2013/070331
§ 371 (c)(1),
(2) Date: Dec. 5, 2014

(87) PCT Pub. No.: WO2013/182721
PCT Pub. Date: Dec. 12, 2013

(65) Prior Publication Data
US 2015/0177126 A1      Jun. 25, 2015

(30) Foreign Application Priority Data
Jun. 7, 2012 (ES) .................................. 201230884

(51) Int. Cl.
*G01Q 20/02* (2010.01)
*G01N 21/17* (2006.01)
(Continued)

(52) U.S. Cl.
CPC ....... *G01N 21/1702* (2013.01); *B81C 99/003* (2013.01); *B82B 3/0085* (2013.01);
(Continued)

(58) Field of Classification Search
CPC ........ B82Y 35/00; G01Q 20/02; G01Q 10/06; B81C 99/003; B82B 3/0085; G01B 21/20; G01H 9/00
See application file for complete search history.

(56) References Cited

U.S. PATENT DOCUMENTS

| | | | | |
|---|---|---|---|---|
| 5,929,440 A * | 7/1999 | Fisher | ........................ | G01J 5/40 250/332 |
| 6,169,281 B1 * | 1/2001 | Chen | ...................... | G01Q 60/38 250/216 |

(Continued)

OTHER PUBLICATIONS

Kosaka, P, et al., "Simultaneous imaging of the topography and dynamic properties of nanomechanical systems by optical beam deflection microscopy" Journal of Applied Physics 109.6 (2011): 064315.*

(Continued)

*Primary Examiner* — Wyatt Stoffa
(74) *Attorney, Agent, or Firm* — Gottlieb, Rackman & Reisman, P.C.

(57) ABSTRACT

Method and system in optical microscopy based on the deflection of micro- and nanomechanical structures, upon impact of a laser beam thereon, which simultaneously and automatically provides a spatial map of the static deflection and of the form of various vibration modes, with vertical resolution in the subangstrom range. The invention comprises at least one mechanical structure, an incident laser beam sweeping the surface of the structure, an optometric detector for capturing the laser beam, and frequency excitation means that generate at least two sinusoidal signals at different frequencies in the mechanical structure.

5 Claims, 5 Drawing Sheets

(51) Int. Cl.

| | |
|---|---|
| G01Q 10/06 | (2010.01) |
| B82B 3/00 | (2006.01) |
| G01B 21/20 | (2006.01) |
| B81C 99/00 | (2010.01) |
| G01H 9/00 | (2006.01) |

(52) U.S. Cl.
CPC ............. *G01B 21/20* (2013.01); *G01Q 10/06* (2013.01); *G01Q 20/02* (2013.01); *G01H 9/00* (2013.01); *G01N 2201/06113* (2013.01)

(56) References Cited

U.S. PATENT DOCUMENTS

| | | | | |
|---|---|---|---|---|
| 7,646,494 | B2* | 1/2010 | Lechuga Gomez ... | G01Q 20/02 250/234 |
| 8,448,261 | B2* | 5/2013 | Passian ................. | G01Q 60/32 850/37 |
| 8,528,110 | B2* | 9/2013 | Humphris .............. | G01Q 20/02 356/28.5 |
| 2006/0072185 | A1* | 4/2006 | Proksch ................ | G01Q 20/02 359/293 |
| 2006/0075803 | A1* | 4/2006 | Boisen ................. | G01N 29/036 73/31.06 |
| 2006/0229842 | A1* | 10/2006 | Vicci ..................... | G01Q 10/06 702/168 |
| 2008/0259356 | A1* | 10/2008 | Lechuga Gomez ... | G01Q 20/02 356/622 |
| 2011/0041224 | A1* | 2/2011 | Raman .................. | G01Q 60/34 850/40 |
| 2013/0117895 | A1* | 5/2013 | Proksch ................ | G01Q 10/00 850/1 |

OTHER PUBLICATIONS

Meyer, Gerhard, and Nabil M. Amer. "Simultaneous measurement of lateral and normal forces with an optical-beam-deflection atomic force microscope." Applied physics letters 57.20 (1990): 2089-2091.*

Mertens, Johann, Mar Álvarez, and J. Tamayo. "Real-time profile of microcantilevers for sensing applications." Applied Physics Letters 87.23 (2005): 234102.*

James S. Burdess et al, "A System for the Dynamic Characterization of Microstructures", Journal of Microelectromechanical Systems, vol. 6, No. 4, Dec. 1, 1997,pp. 322-328.

P.M. Kosaka, et al., "Simultaneous Imaging of the topography and dynamic properties of nanomechanical systems by optical beam deflection microscopy"; Journal of Applied Physics 109, No. 6, 064315 (2011—American Institute of Physics), pp. 064315-1 to 064315-5).

Murali Krishna Ghatkesar et al., "Higher modes of vibration increase mass sensitivity in nanomechanical microcantilevers", Nanotechnology vol. 18 (Jul. 2007), No. 44, 445502 (8pp), IOP Publishing.

Si Dongsen et al., "Research of Auto-Tracing System Based on PSD1", ISEP,Computer Science Applications and Education, vol. 1 No. 2 Oct. 2011, pp. 11-14; <URL: http://isctae.org/paper-isctae/English/v1n2/2q201203.pdf>.

Ramos D. et al., "Photothermal excitation of microcantilevers in liquids", Journal of Applied Physics 99, No. 12, 124904 (2006), American Institute of Physics, pp. 124901-1 to 124901-8.

International Search Report for PCT/ES2013/070331 dated Oct. 28, 2013.

Kosaka P.M. et al: "Simultaneous imaging of the topography and dynamic properties of nanomechanical systems by optical beam deflection microscopy", Journal of Applied Physics, American Institute of Physics, US, vol. 109, No. 6, Mar. 24, 2011, pp. 64315/1-64315/5.

European Search Report for corresponding application EP 13799806.8 dated Dec. 17, 2015.

* cited by examiner

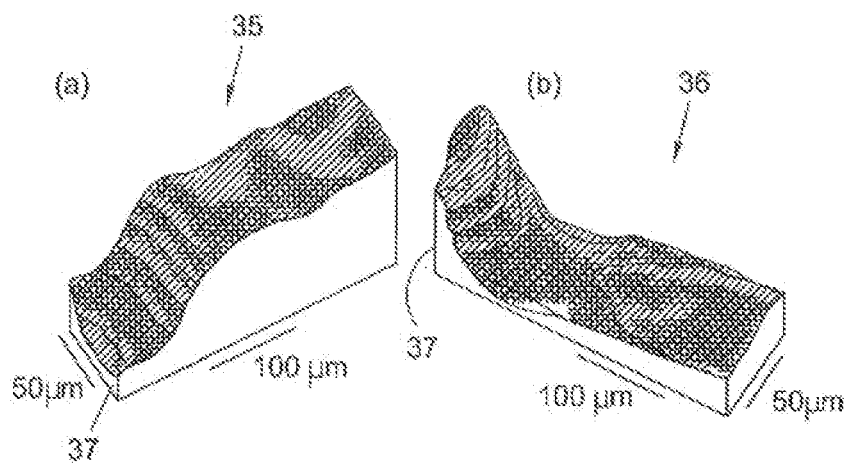
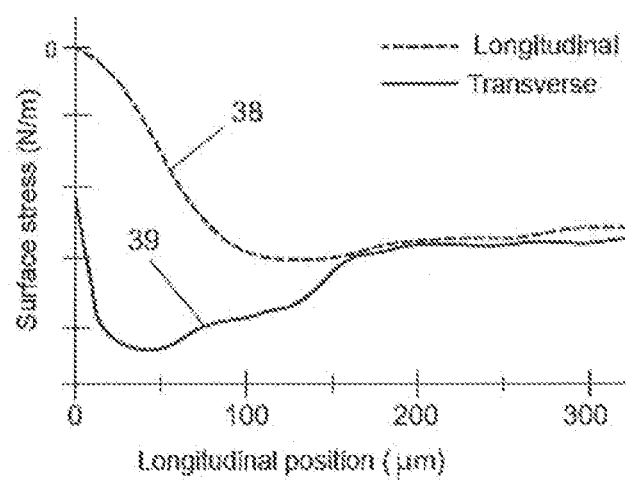
FIG. 5
FIG. 6

METHOD AND SYSTEM FOR CHARACTERIZATION OF NANO- AND MICROMECHANICAL STRUCTURES

This application is the U.S. National Stage application of PCT/ES2013/070331 filed May 23, 2013, which claims priority from ES application P201230884 filed Jun. 7, 2012.

OBJECT OF THE INVENTION

The present invention first relates to a method for characterization of nano and micromechanical structures, and also to a system for carrying out the described method. Said characterization is carried out by means of excitation of the nano- and micromechanical structures by means of a laser beam, excitation of the structures with signals at different frequencies and measurement of the different parameters depending on the reflected laser beam. The field of application of the present invention is the field of characterizing the mechanical response of nano- and microstructures.

BACKGROUND OF THE INVENTION

Miniaturization of mechanical devices at the micro- and nanoscale, referred to as micro- and nanomechanical systems (MEMS and NEMS, Microelectromechanical Systems and Nanoelectromechanical Systems, respectively), has allowed the development of advanced scanning technologies of mechanical sensors and is quite relevant in the fields of electronics and power generation. The potential of these systems is based on the fact that displacement on the nanometric scale and vibration of such system is very sensitive to external forces, farces generated on the surface plane thereof and the mass added thereon. These attributes mean that micro- and nanomechanical systems combined with optical or electric displacement sensors can be applied in detecting the force between two molecules or atoms, with a sensitivity in the attonewton range, and for measuring a deposited mass with a sensitivity in the zeptogram range, and at the same time finding the elastic constant, with kilopascal resolution; or for detection applications without surface molecular markers through the generated forces. MEMS and NEMS have also been used as high-precision radio frequency filters, accelerometers and gyroscopes.

In the current state of the art, cantilever-based micro- and nanomechanical systems are known to have a fixed end and a mobile end. The placement and/or motion of the free end are what are normally detected in these systems. Cantilever-based systems fixed at both ends, of the type in which the motion of the central part thereof can be detected are also well-known.

Hereinafter, when discussing the general background of the invention, reference will be made to cantilevers having a fixed system and a free system, the deflection of which must be measured (deflection refers to displacement of the free end of the microcantilever) in response to light, but advancements in such architectures are also applicable to other previously mentioned designs.

When cantilevers are reproduced at the microscale, conventionally with a thickness of 0.2-1 µm, width between 100-500 µm and length of 100-500 µm; such cantilevers can bend in the order of a few nanometers in response to forces in the piconewton range. It is in this range where forces between atoms, molecules and biomolecules governing many of the physicochemical properties of materials, as well as many fundamental life processes, converge. The corresponding deflections of microcantilevers can be optically and electrically detected with a resolution of at least 100 pm/Hz1/2.

Generally, there are various techniques for reading the deflection of the cantilever, such as capacitive sensing, tunneling current sensing, optical interferometry, piezoresistive reading, as well as the so-called optical beam deflection techniques. The latter is the most widely used method due to its simplicity, enormous sensitivity and its ability to measure in air, mixtures of gases and fluids without contacting displacement sensors or the reading circuitry.

As previously mentioned, the optical beam deflection method is very sensitive and has the advantage that it can be readily implemented. A segmented photodetector split into two segments oriented parallel to the axis of motion of the cantilever is normally used for capturing the reflected beam. Deflection of the cantilever causes displacement of the laser dot reflected on the photodetector. The difference in photocurrents between the two segments is therefore proportional to the deflection of the cantilever.

In addition to static deformation, resonance frequencies of micro- and nanostructures for soft surface scanning in AFM and for the development of sensors which are based on the addition of masses and the rigidity of the molecules captured on the surface of the cantilevers have been measured. Cantilevers are usually considered to be structures having a unique resonance frequency (fundamental resonance frequency), exciting them to frequencies close to the resonance frequency; however mechanical structures have several modes of vibration at higher frequencies than the fundamental frequency.

There is growing interest in the use of high frequency modes to increase sensitivity and detection limits. However, it is extremely complex to determine the mode shape at frequencies corresponding to resonance frequencies, which is very important for quantifying and interpreting the measurements. Knowledge about the shape of modes of vibration and the accurate measurement of corresponding frequencies is extremely relevant for the design of MEMS and NEMS in all fields of application.

There are also issues concerning the dynamic behavior of cantilevers that have not been resolved, such as: the effect of the surface stress on resonance properties or coupling between modes of vibration induced by viscous damping, elastic elements or by intermittent contact. The emergence of finite element simulations and the ever-increasing computer processing speed shed light on these issues. However, these simulations are very time-consuming and ignore defects and flaws inherent to micro and nano manufacturing processes. On the other hand, the free parameters in the simulation, such as grid size or the definition of contour conditions and pre-stressing conditions of the structure cannot always be chosen or determined in a realistic manner, so simulations can only serve as a guide in the design of MEMS and NEMS but not as a tool capable of realistically simulating the behavior of these structures. The experimental measurement of the shape of modes of vibration and the determination of their frequencies is a critically necessary tool; this tool is the object of the present invention.

Recently, scanning Doppler laser vibrometry (SDLV) [Biedermann L B et al. (2009) "Flexural vibration spectra of carbon nanotubes measured using laser Doppler vibrometry"] and phase-shifting interferometry [Kelling S. et al. (2009) Simultaneous readout of multiple microcantilever arrays with phase-shifting interferometric microscopy"] (WLI, White Light Interferometry) have demonstrated a significant ability for characterization of nanomechanical systems. SDLV can obtain images with high sensitivity with respect to vibration, outside the plane of these systems in the sub-angstrom range and with submicrometric lateral resolution. WLI provides information about topography with a vertical resolution of 1-10 nm. Additionally, implementation of the stroboscopic lighting in WLI has allowed mode of vibration analysis, although the process is slow, bandwidth is limited and resolution is still insufficient.

Therefore, despite the existing state of the art techniques that can provide simultaneous information about the static and dynamic behavior of nanomechanical systems with high sensitivity in a rapid and simple manner are still needed.

Specifically, the most widely used systems today for dynamic motion/displacement analysis, WU LDVP (Laser Doppler Vibrometer) cannot simultaneously obtain information about the motion of the micro- or nanostructure, static deformation and motion at various vibration frequencies, more scans being necessary, one in each frequency scenario.

Additionally, although these techniques may be practical for measuring the motion/displacement of individual elements, many practical uses of the systems for measuring micro- and nanomechanical elements require the use of arrays having a large number of micromechanical elements comprising a plurality of cantilevers arranged in a certain formation and operating in parallel, therefore providing greater speed and multifunctionality. This invention proposes that laser beam deflection systems are suitable for measuring both static and dynamic behavior of elements/cantilevers, for example: maximum deflection, mean deflection value, the amplitude at a reference frequency (the element can be excited externally by means of an excitation force that oscillates at a reference frequency), a phase of motion with respect to an excitation signal, a frequency, etc. Measured static displacement, amplitude, frequency, etc., can be related to an object that must be measured and interacts with the cantilever, and to the signals used to stimulate the object and/or cantilever.

Although the optical beam deflection technique can resolve deflections of up to 0.1 nm, implementation of this technique for reading in microcantilever arrays is a complex subject, such that there is no system, technique or method that allowed obtaining the response of several alignments of micro- and nanomechanical systems at different frequencies simultaneously. The present invention provides an optical microscopy technique based on the beam deflection method which simultaneously and automatically provides a spatial map of the static deflection and of the shape of five modes of vibration, with vertical resolution in the sub-angstrom range.

DESCRIPTION OF THE INVENTION

The present invention first relates to a method for characterization of nano- and micromechanical structures. To that end, the present invention makes use of at least one mechanical structure that could be a nanomechanical structure or a micromechanical structure. Said mechanical structure could be formed by one or more layers, each of said layers being of different materials. Furthermore, there could also be layers of, for example, oxide on metallic layers which must be taken into account when carrying out the method for characterization, considering them as another layer of the structure. The application of the mentioned method to an array of mechanical structures made up of nanomechanical structures, micromechanical structures and a combination thereof has also been envisaged. Therefore, the method object of the present invention comprises the following steps:

defining a coordinate system in which the X- and Y-axes correspond to the surface plane of the mechanical structure;

exciting the mechanical structure by means of a signal made up of at least two sinusoidal signals at different frequencies;

automatically scanning the surface plane of the mechanical structure by means of a laser beam;

capturing a laser beam reflected off the surface plane of the mechanical structure by means of an optical or optometric detector previously placed in the path of the reflected beam obtaining slope vectors in the X plane and in the Y plane of the surface plane of the mechanical structure;

performing a fast Fourier transform on the slope vectors in the X and Y planes;

defining a mask based on the intensity of the reflected laser beam;

applying the mask to dynamic components of the slope vectors in the X and Y planes, a normal data vector normal to the static surface plane and multifrequency being obtained; and reconstructing a topography and a shape of the at least two modes of vibration by means of a method for iterative two-dimensional integration of the normal data vector.

In a particular embodiment of the invention, it has been envisaged that the at least two sinusoidal signals used to excite the mechanical structure have a frequency coinciding with the mode of vibration frequencies of the mechanical structure.

In another embodiment of the invention, it has been envisaged that the method for iterative two-dimensional integration is a method for image reconstruction in photometric stereography.

In another embodiment of the invention, excitation of the mechanical structure comprises being performed by means of a piezoelectric actuator placed in contact with the mechanical structure such that said actuator directly transmits excitation to the structure.

In another embodiment of the invention, excitation of the mechanical structure is performed by heating the layers forming the mechanical structure by means of a heating element, causing vibration of the structure. The mechanical structure is therefore heated and cooled at the frequencies of choice to cause the expansion/shrinkage of the mechanical structure. In this particular case, the structure must be formed by at least two layers of different materials, because as the two materials responding differently to temperature, forces are generated between the layers that cause excitation of the assembly of the mechanical structure.

Nevertheless, there are a considerable number of techniques for exciting the mechanical structure and they are well-known in the state of the art, some examples of such techniques being: optothermal excitation, acoustic excitation, piezoelectric excitation, magnetic excitation, etc.

A second object of the present invention is a system for characterization of nano- and micromechanical structures for carrying out the method described above. Said system at least comprises:

at least one mechanical structure selected from a nanomechanical structure, a micromechanical structure, parts thereof and a combination thereof;

a laser for emitting a laser beam onto the mechanical structure;

guiding means for guiding the mechanical structure on the X- and Y-axes, the X- and Y-axes being the axes defining the surface plane of the mechanical structure;

an optometric detector for capturing the laser beam that is reflected on the mechanical structure; and frequency excitation means generating at least two sinusoidal signals at different frequencies in the mechanical structure.

Therefore, the system object of the present invention uses the beam deflection technique which can simultaneously detect static deflection/deformation and the shape of several modes of vibration of a plurality of elements, these elements preferably being; micro- and nanomechanical elements or parts thereof, with vertical resolution in the sub-angstrom range in a single measurement.

In a preferred embodiment of the system, the mechanical structure is a cantilever selected from a microcantilever and a nanocaritilever.

In another embodiment of the invention, the optometric detector is a two-dimensional linear position detector.

In another embodiment of the invention, the system comprises current-voltage amplifiers converting currents generated in the position detector into the output voltage on the X-axis, the output voltage of the Y-axis and the voltage of the intensity of the reflected beam.

In another particular embodiment of the invention, the frequency excitation means is selected from a piezoelectric actuator and thermal excitation means. It can be seen that the excitation means will depend, in any case, on the technique selected from among those belonging to the state of the art for generating excitation of the mechanical system. In a more preferred embodiment, the thermal excitation means are a frequency modulated laser focused on a surface of the mechanical structure. For carrying out the frequency excitation of the mechanical structure using thermal means, the mechanical structure must be formed by at least two layers of different materials.

The present invention has preferably been envisaged for use with cantilever-based micro- and nanomechanical systems having a fixed end and a mobile end. Nevertheless, the present invention can also be applied in a similar manner to other mechanical elements such as cantilever-based systems fixed at both ends, of the type in which the motion of the central part thereof can be detected. It is also applied to other micro- and nanomechanical structures that are able to move, become deformed or that are flexible, such as drums, membranes, cavities, flanges, etc. The present invention has also been envisaged for use in silicon nanowires, which are usually the extension of the cantilevers on a small scale, or surface acoustic wave (SAW) and bulk acoustic wave (BAW) microsystems, where the present invention can be used to measure deformation of the active, piezoelectric material; and generally another type of micro- or nanosystem where change in reflectivity, deformation, stress or motion takes place, such as a disc-shaped micromirror or transparent, translucent or opaque prism presenting a change in reflectivity when illuminated, or a multilayer structure.

BRIEF DESCRIPTION OF THE DRAWINGS

FIGS. 5a and 5b show three-dimensional depictions of the longitudinal components (a) and transverse components (b) of the surface stresses generated on the surface of the cantilever of FIG. 4 derived from its curvature.

FIG. 6 shows the profiles of longitudinal and transverse surface stresses along the longitudinal axis of the cantilever shown in FIGS. 5a and 5b.

DESCRIPTION OF SEVERAL EMBODIMENTS OF THE INVENTION

Figure 1:
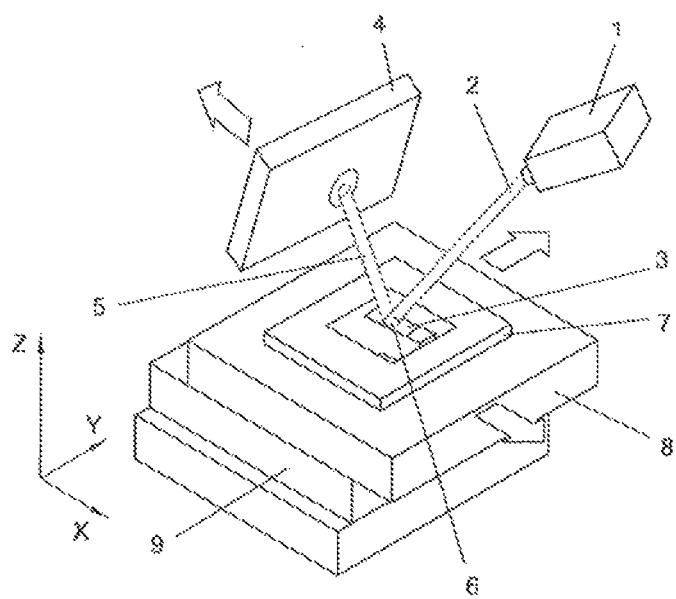
FIG. 1 shows an embodiment of the system for characterization of the displacement of the end of a microcantilever, object of the present invention.

An illustrative and non-limiting description of several embodiments of the invention is provided below in reference to the reference numbers used in the drawings.

As shown in FIG. 1, the method and system object of the present invention is based on automatic two-dimensional scanning of a highly focused laser beam through the surface of a mechanical system, for example a microcantilever system, and the capture of the beam reflected on the surface of the two-dimensional PSD oriented orthogonally with respect to the reflected ray.

A conventional arrangement of the elements for measuring optical beam deflection is schematically shown. A light source (1) (usually a laser) emits a light beam (2) focused (directly or by means of using intermediate optical elements, such as mirrors) on the mechanical structure (3), the displacement of which is to be measured, for example, on the end of a cantilever (3). The fixed end of the cantilever (3) is anchored to a piezoelectric actuator (7). Deflection of the reflected beam (5) is preferably measured with an orthogonal PSD (4), but a segmented photodetector, a continuous position detecting photodetector, an array of photodetectors, etc., could also be used.

Therefore, a coordinate system where the X-Y plane is the plane of the surface of the microcantilever (3) and X and V are along the scanning directions of the beam (2), is first defined. Therefore out-of-plane displacement of the cantilever (3) occurs along the Z-axis. The incident beam (2) is in the X-Z plane, and the photodetector (4) is oriented with an axis along the Y direction. With this configuration, photocurrents along the axes of the photodetector (4) (determined by the coordinates of the reflected laser beam (5) in the photodetector (4)) are linearly proportional to the slope of the cantilever (3) along the X and Y directions in the point of reflection (6). In turn, in order for the beam (2) to scan the surface of the cantilever (3), it has been envisaged that the piezoelectric actuator (7) is fixed to a first micropositioner (8) which travels in the X-Z plane and which in turn travels over a second micropositioner (9) which travels in the Y-Z plane.

Figure 2A:
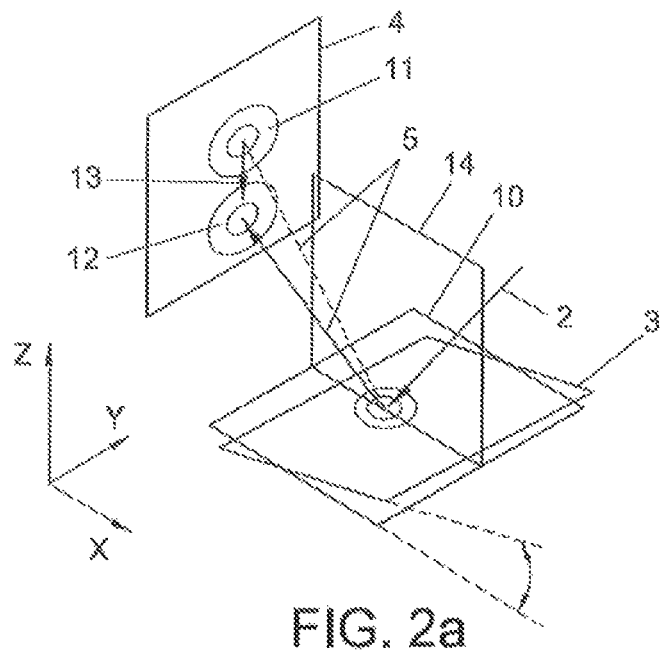
FIGS. 2a and 2b show a schematic depiction of the displacement of the reflected laser beam in a two-dimensional linear position detector (PSD, acronym for photo sensitive detector) due to the change in slope displayed along the X- and Y-axes of the microcantilever, respectively.
Figure 2B:
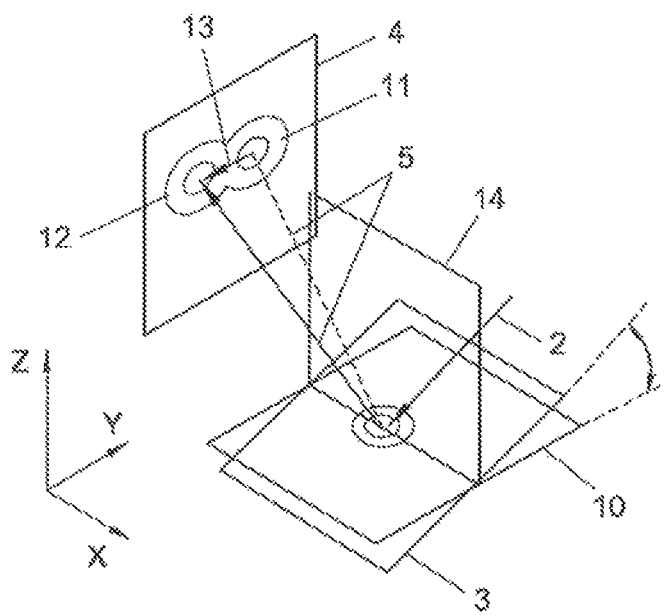

FIG. 2a shows the deflection of the microcantilever (3) with the displacement thereof in the X-Z plane (14) as the laser beam (2) strikes it. Displacement of the reflected beam (5) on the Z-axis due to deflection of the microcantilever (3) is seen in the photodetector (4), because said microcantilever (3) is initially located in the X-Y plane (10), the reflected beam (5) striking at a first point (11) of the photodetector (4). Then due to the incidence of the beam (2) at the point of reflection (15), the cantilever (3) leaves the X-Y plane, the reflected beam (5) traveling on the Z-axis to a second point (12) of the photodetector (4). Displacements (13) of the reflected beam (5) due to deflection of the microcantilever (4) can therefore be easily measured. FIG. 2b shows another embodiment in which deflection of the microcantilever (4) generates displacement (13) of the reflected beam (5) in the photodetector on the Y-axis.

Figure 3:
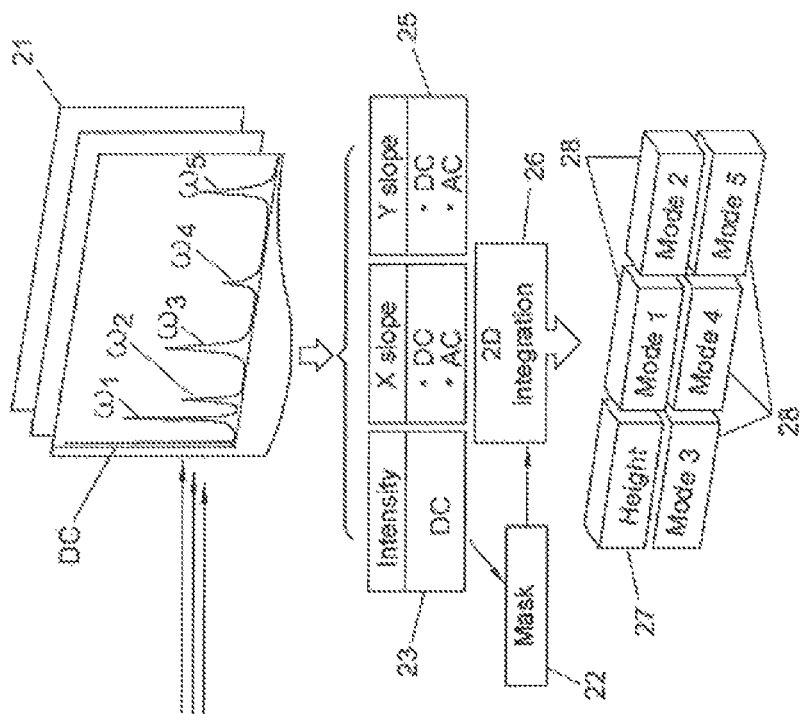
FIG. 3 shows a schematic depiction of an embodiment of the method for characterization for multifrequency excitation/detection, object of the present invention.
Figure 3:
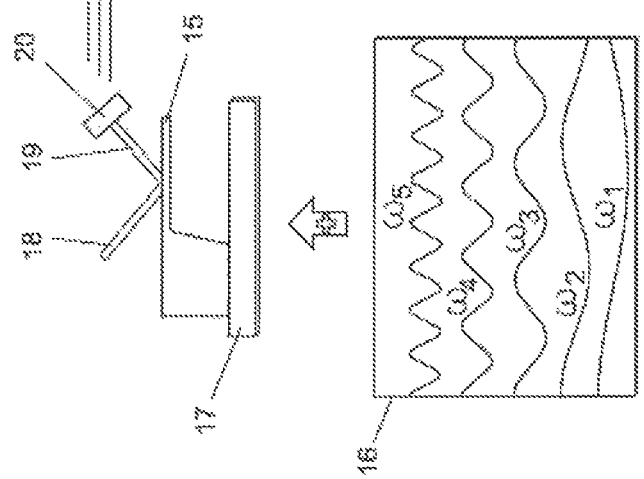

FIG. 3 shows an embodiment of the method and system described in the present invention. To obtain real data about the dynamic behavior of a cantilever (15), said cantilever (15) is excited by a signal (16) made up of the sum of five time-dependent sinusoidal signals at different frequencies ($w_1$-$w_5$). These signals are chosen such that their frequencies coincide with the frequencies of the modes of vibration, and the amplitude of each frequency component is tuned to obtain similar responses with respect to amplitude in the cantilever (15). The signal (16) is applied through a piezoelectric bimorph (structure formed by two layers of two active materials) (17) located close to the base of the cantilever (15). The method can be extended to more frequencies but five frequencies have been chosen to limit the amount of data generated.

Once the incident beam (18) is projected onto the microcantilever (15) and the reflected beam (19) is digitally captured by a tuned amplifier integrated in the photodetector (20), the raw data of the signals of the slopes of the photodetector (20) are multiplexed in static and quadrature amplitudes for each frequency component of the excitation signal (16). Therefore, 23 images (21) are obtained for five frequencies ($w_1$-$w_5$) in a single scan: static X and Y slopes; and the reflectivity; and the phase and quadrature amplitudes of X and Y slopes at the five excitation frequencies ($w_1$-$w_5$).

After the beam (18) scans the cantilever (15), the system defines a mask (22) based on the continuous component (23) of the intensity of the reflected light beam (19) which gives the shape of the cantilever (15). This mask (22) is applied to the dynamic components of the X slope (24) and V slope (25) to obtain the normal vector normal to the surface of the static cantilever (15) and multifrequency. To reconstruct the topography (27) and the shape of the five excited modes of vibration (28), a method for two-dimensional integration (26) used for reconstructing the image in photometric stereography to calculate the height through the normal data vector is used.

Embodiments are described below in which experiments have been conducted on commercial microcantilevers to obtain their resonance frequencies, mode shapes and surface stress. To demonstrate that the technique produces correct results, finite element simulations have been performed to verify the concept and the capacity of the method and of the system, all of which are objects of the present invention.

Therefore, in a particular embodiment a technique is applied for determining the spatial distribution of surface stress and the mode shape (the physical shape of the structure at normalized resonance frequency) of the first 22 normal modes of vibration of a commercial sensor with eight gold-plated cantilevers (Concentris®). The dimensions of the cantilevers are 500 µm in length, 100 µm in width and 1 µm in thickness.

The photocurrents are converted into voltages through current-voltage amplifiers integrated in the photodetector to obtain three output voltages which give the X and Y slopes of the surface and the intensity of the reflected laser beam. Since the photocurrents are normalized with respect to the total photocurrent, the values of the slopes are not sensitive to fluctuations in intensity and variations in surface optical properties. The cantilever was oriented along the X direction in the experiments, such that variations in X and V slope channels can be related to the bending and twisting motion of the cantilever.

The excitation signal of the sensor used consists of the sum of five signals at different frequencies. The frequencies are chosen such that they coincide with the resonance frequencies of different modes of vibration. A fast Fourier transform of the PSD channels corresponding to the slope in X and to the slope in Y of the sample shows out-of-plane static and multimode displacements. PSD channel intensity is used as a mask to obtain the shape of the cantilever. A method for iterative integration is used to reconstruct the topography and the shape of the five modes of vibration.

Figure 4:
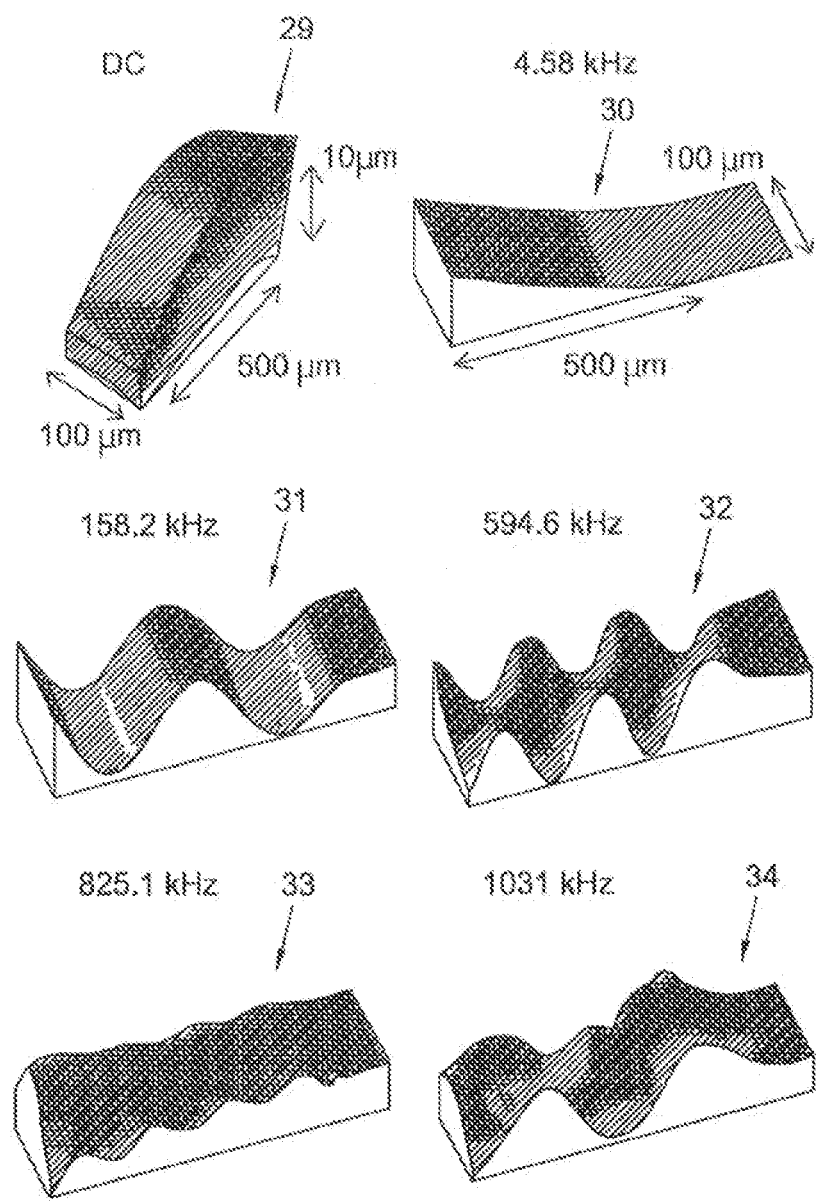
FIG. 4 shows the three-dimensional depiction of an embodiment of the out-of-plane static displacement and the shape of five modes of vibration of a microcantilever sensor.

FIG. 4 shows the topography resulting from the shape of the cantilever (29) and the shape of five modes of vibration (30-34) obtained in a single scan of the invention consisting of 512 lines at a rate of one line per second. The acquisition time per pixel is about 2 ms. The topography data shows that the cantilever (29) is bent downwards (from the gold-plated face to the silicon-coated face) about 22 µm. This bending is the result of high residual compressive stress developed during thermal evaporation of a 50 µm layer of gold. The five excitation frequencies, 4.58 kHz, 158.2 kHz, 594.6 kHz, 825.1 kHz and 1031 kHz, correspond to normal modes of vibration 1, 6, 14, 17 and 22, respectively, of the cantilever. A notable feature of the technique is the large frequency range, from a few kHz up to 1 MHz, shown in dynamic characterization. This range can be even further increased by improving the bandwidth of the PSD reading electronics. It is important to point out that although the use of high modes of vibration is advantageous (in terms of sensitivity due to both higher frequency and the quality factor), knowing the shape of the mode of vibration is absolutely necessary for obtaining quantitative measurements.

FIG. 5 shows quantitative measurements of the calculation of residual surface stress of the cantilever described in FIG. 4, which demonstrate how advantageous the present invention is.

The two-dimensional spatial distribution of the surface stress was derived by calculating the local curvature and applying the Euler-Bernoulli ratio between torque and curvature. FIGS. 5(a) and 5(b) show the spatial map of the longitudinal components (35) and transverse components (36) of the surface stress. The cantilever is anchored on one of the short sides (37) of the representation of the spatial maps shown. The profiles of the longitudinal surface stress (38) and transverse surface stress (39) along the longitudinal axis of the cantilever are shown in FIG. 6. The images in FIGS. 5(a) and 5(b) have a length of 320 µm and a width of 70 µm. This size has been chosen in order to indicate the cantilever region close to the cantilever where there are non-uniform curvatures and in order to exclude the edges of the cantilever where the curvature measurement is very noisy.

The results clearly show that surface stress is neither uniform nor isotropic through the cantilever. The absolute value of longitudinal surface stress is maximum close to the anchoring and decreases to a constant value at a distance from the anchoring of about twice the width of the cantilever.

The noise of the curvature measurement due to the inherent noise produced in numerical derivatives is highlighted. In this context, deflection of the scanning laser beam has advantages for quantifying plane stresses in micromechanical structures. However, when out-of-plane displacement is measured directly, as in the case of the interferometric measurements, calculating the curvature requires the second derivative of measurement, giving rise to two-step amplification noise. More advantageously, the beam deflection technique directly measures slope, so it reduces the steps of numerical derivation to one. Furthermore, the beam deflection technique is extremely sensitive, with noise below 100 pm/Hz1/2, which is about ten times lower than the noise of the white light interferometry systems, which is the standard technique used for making images experience out-of-plane static displacements in micromechanical structures.

In another embodiment of the invention, the experimental mode shape obtained by means of the method for characterization of micro- and nanomechanical structures object of the present invention has been compared to a simulation by means of the finite element method. To that end, the first 22 modes of a microcantilever sensor have been characterized.

Normal mode frequencies and shapes of microcantilevers were simulated by means of the finite element method (FEM, acronym for finite element modeling) using the Comsol 4.2 commercial software package. A gold-plated microcantilever with a length of 500 µm, width of 100 µm, and substrate and coating thickness of 950 nm and 50 nm, respectively (nominal dimensions of the microcantilevers used in the experiments), was simulated.

The simulation process consisted of two sequential steps. First, the static voltages of the cantilever when said cantilever is subjected to a uniformly distributed change in temperature were calculated. The temperature value was chosen so as to get the cantilever to bend due to the bi-metal effect, similar to that found experimentally by the stress generated in the gold plating. The simulation included the effects of large deformation which emerge from geometric non-linearities.

Therefore, the Green strain tensor and the second Piola-Kirchhoff stress tensor are used, and the solution is achieved by using total Lagrangian formulation. In the second step of the simulation, frequencies per se were obtained, including static deformation of the cantilever previously obtained in the first step of the simulation. A convergence study was conducted by fine tuning the elements of the grid until the relative error in the normal frequency of the cantilever was below $10^{-4}$. This corresponds to a grid consisting of about 500000 elements.

As indicated in the preceding embodiment, the gold-plated face of the microcantilevers has considerable residual stress giving rise to significant bending of the cantilever. In order to compare experiments with rigorous FEM simulations, the effect of surface stress has been introduced in the simulations. Said simulations show that even though the surface stress barely modifies the vibration of the mode of vibration in these conditions, it does induce a significant change in the frequency of the modes of vibration, said change depending on the type of mode (bending, twisting and U-shaped). Therefore, the theoretical frequency with respect to the frequency obtained by means of the simulation shows less than a 5% deviation for the six first modes of vibration, increasing up to 10% for U-shaped modes of vibration.

These results show the ability of the present technique to rapidly obtain the multimode shape of the vibration of micro- and nanomechanical systems and the capacity to combine this dynamic behavior with the stress/voltage field of the mechanical system.

The invention claimed is:

1. A method for characterization of nano- and micromechanical structures, comprising at least one mechanical structure selected from a nanomechanical structure and a micromechanical structure, the mechanical structure being formed by at least one layer, where each layer is of a different material, characterized in that it comprises the following steps:
defining a coordinate system in which the X- and Y-axes correspond to a surface plane of the mechanical structure;
exciting the mechanical structure by means of a signal made up of at least two sinusoidal signals at different frequencies;
automatically scanning the surface plane of the mechanical structure by means of a laser beam;
capturing a laser beam reflected off the surface plane of the mechanical structure by means of an optical/optometric detector previously placed in the path of the reflected beam obtaining slope vectors in an X plane and in a Y plane of the surface plane of the mechanical structure;
performing a fast Fourier transform on the slope vectors in the X and Y planes;
defining a mask based on the intensity of the reflected laser beam;
applying the mask to dynamic components of the slope vectors in the X and Y planes, to obtain a normal data vector normal to the static surface plane and multifrequency; and
reconstructing a topography and a shape of at least two modes of vibration by iterative two-dimensional integration of the normal data vector.

2. The method for characterization of nano- and micromechanical structures according to claim 1, characterized in that the at least two sinusoidal signals have a frequency coinciding with mode of vibration frequencies of the mechanical structure.

3. The method for characterization of nano- and micromechanical structures according to claim 1, characterized in that the iterative two dimensional integration is image reconstructed as practiced in photometric stereography.

4. The method for characterization of nano- and micromechanical structures according to claim 1, characterized in that excitation of the mechanical structure comprises being performed by means of a piezoelectric actuator placed in contact with the mechanical structure, directly transmitting excitation thereto.

5. The method for characterization of nano- and micromechanical structures according to claim 1, characterized in that excitation of the mechanical structure is performed by heating the at least one layer forming the mechanical structure by means of a heating element.

\* \* \* \* \*